United States Patent
Eger et al.

(10) Patent No.: US 7,882,835 B2
(45) Date of Patent: Feb. 8, 2011

(54) DEVICE AND METHOD FOR DETERMINING LEAKS OF A RESPIRATOR

(75) Inventors: Marcus Eger, Luebeck (DE); Dieter Weismann, Gross Groenau (DE)

(73) Assignee: Dräger Medical GmbH, Lübeck (DE)

( * ) Notice: Subject to any disclaimer, the term of this patent is extended or adjusted under 35 U.S.C. 154(b) by 965 days.

(21) Appl. No.: 11/554,905

(22) Filed: Oct. 31, 2006

(65) Prior Publication Data

US 2007/0144522 A1 Jun. 28, 2007

(30) Foreign Application Priority Data

Dec. 22, 2005 (DE) .................. 10 2005 061 439

(51) Int. Cl.
  *A62B 7/04* (2006.01)
  *F16K 31/26* (2006.01)
(52) U.S. Cl. .................. 128/204.26; 128/200.24; 128/204.18
(58) Field of Classification Search ............ 128/204.26, 128/205.23, 204.18, 200.24, 204.21, 204.23
See application file for complete search history.

(56) References Cited

U.S. PATENT DOCUMENTS

| | | | |
|---|---|---|---|
| 6,059,732 A * | 5/2000 | Orr et al. ................ 600/532 |
| 6,536,432 B2 * | 3/2003 | Truschel ................ 128/205.23 |
| 6,626,175 B2 * | 9/2003 | Jafari et al. ............ 128/204.21 |
| 6,659,101 B2 | 12/2003 | Berthon-Jones | |
| 7,448,382 B1 * | 11/2008 | Alexander et al. ...... 128/204.18 |
| 7,475,685 B2 * | 1/2009 | Dietz et al. ............ 128/204.23 |
| 7,562,657 B2 * | 7/2009 | Blanch et al. .......... 128/204.23 |
| 2004/0074492 A1 * | 4/2004 | Berthon-Jones ........ 128/200.24 |
| 2004/0211422 A1 * | 10/2004 | Arcilla et al. .......... 128/204.19 |
| 2005/0241639 A1 * | 11/2005 | Zilberg .................. 128/204.21 |

\* cited by examiner

*Primary Examiner*—Steven O Douglas
*Assistant Examiner*—Colin Stuart
(74) *Attorney, Agent, or Firm*—McGlew and Tuttle, P.C.

(57) ABSTRACT

A method, system and device are provided for the determination of leaks in a respirator. An inspiraton pressure $p_{insp}$ is recorded during an inspiration time $T_{insp}$ with a measuring device. The inspiration pressure $p_{insp}$ is varied during consecutive breaths I. Leaks are determined as to leak volumes $V_{Li}$ from the product of $p_{inspi}$ and $T_{inspi}$ in accordance with the equation $$V_{Li} = A \times p_{inspi}^{B} \times T_{inspi}$$

while the parameters A and B are determined in an analyzing unit by a regression model with $p_{insp}$ as the regressor.

8 Claims, 5 Drawing Sheets

DEVICE AND METHOD FOR DETERMINING LEAKS OF A RESPIRATOR

CROSS REFERENCE TO RELATED APPLICATIONS

This application claims the benefit of priority under 35 U.S.C. §119 of German Patent Application DE 10 2005 061 439.6 filed Dec. 22, 2005, the entire contents of which are incorporated herein by reference.

FIELD OF THE INVENTION

The invention relates to respirators (also known as ventilators) generally and more particularly to a method, system and device for the determination of leaks in a device for supplying a patient with breathing gas, which has at least one analyzing unit and one measuring device for determining the respiratory tract pressure.

BACKGROUND OF THE INVENTION

In almost all respirators, leaks can occur, which are either system-related, as a result of a mask that has not been put on tightly enough, or patient-related, for example, in the form of a fistula. This leak generally depends on the positive pressure respiration and on the respiration method used. A distinction is to be made here between pressure-controlled and volume-controlled respiration.

In volume-controlled respiration, the inspiration takes place as predetermined by the stroke volume and by the time curve of the volume flow, and the respiratory tract pressure is dependent upon the volume flow and the stroke volume. The level of the respiratory tract pressure essentially depends on the lungs of the patient and also on the breathing efforts of the patient. In the volume-controlled respiration, it is necessary to monitor the upper respiratory tract pressure in order to prevent a lung of the patient from becoming damaged due to too high pressures. The rigid predetermination of the time curve of the volume flow has a problematic effect, if the patient develops his/her own activity during the breathing and thus wants to determine the volume flow himself/herself.

Pressure-controlled respiration takes place as predetermined by the time curve of the respiratory tract pressure. In this case, so much breathing gas is supplied until a predetermined respiratory tract pressure is reached. In pressure-controlled respiration, the volume flow and the stroke volume are monitored. If the breathing gas for respirating a patient is provided via a fan as a pressure source, then the respiration usually takes place as predetermined by the pressure curve, since the respiratory tract pressure, but not the volume flow can be adjusted via a regulation of the speed of the fan in a relatively simple way. The possibility of also predetermining the stroke volume here is desirable.

To compensate for a leak in pressure-controlled respiration, a so-called compensating gas flow is added, so that the respiratory tract pressure can be maintained at the preselected pressure level.

In the volume-controlled respiration, the added compensating gas flow should be included in the calculation of the stroke volume. The compensation for a leak by means of adding a compensating gas flow also interferes with the setting of the trigger thresholds, with which an inspiration stroke is triggered.

Since the system leak has different effects on the system functionalities of the respirator, accurate knowledge thereof is important in order to be able to make a suitable compensation. In the prior-art respirators, usually a linear or square root dependence of the leak is based on the respiration pressure.

A square root dependence between a leak and the respiration pressure for a respirator with a fan emerges, for example, from U.S. Pat. No. 6,659,101 B2.

The drawback in this case is that a characteristic curve limited to the square root function can only approximate the different leak forms approximately.

SUMMARY OF THE INVENTION

The object of the present invention is thus to provide an improved method for leak compensation and a device for carrying out the method.

According to the invention, a method is provided for the determination of leaks in a device for supplying a patient with breathing gas. The device has at least one analyzing unit and one measuring device for determining the respiratory tract pressure. The method includes recording an inspiration pressure $p_{insp}$ during an inspiration time $T_{insp}$ with the measuring device and varying the inspiration pressure $p_{inspi}$ during consecutive breaths I. Next the method includes determining leak volumes $V_{Li}$ from the product of $p_{inspi}$ and $T_{inspi}$ in accordance with the equation $$V_{Li} = A \times p_{inspi}^B \times T_{inspi}$$

while the parameters A and B are determined in the analyzing unit by a regression model with $p_{insp}$ as the regressor.

The method may also include adding an additive term $\epsilon_i$, which takes irregular breathing of the patient into consideration, to the equation for $V_{Li}$.

Further, the method may also include the step of additionally taking into account the end expiratory pressure peep as another regressor and thus allowing variable expiratory pressures according to the equation $$V_{Li} = A(p_{inspi}^B \cdot T_{inspi} + peep_i^B \cdot T_{exspi}) + \epsilon_i.$$

According to another aspect of the invention a system and device are provided for the determination of leaks in a device for supplying a patient with breathing gas. The device includes a means for producing a respiratory pressure curve, a means for switching between an inspiration phase and an expiration phase as well as a measuring device for recording an inspiration pressure $p_{insp}$. A means is provided for describing leak volumes $V_{Li}$ from the product of $p_{inspi}$ and $T_{inspi}$ in accordance with the equation $$V_{Li} = A \times p_{inspi}^B \times T_{inspi}$$

with the parameters A and B to be determined by a regression calculation. A means is provided for determining the leak flow $\dot{V}_L(t)$ from the positive pressure respiration curve $p(t)$ according to the equation $$\dot{V}_L(T) = A \cdot p^B(t)$$

with the parameters A and B to be determined by a regression calculation.

According to the present invention, instead of a arbitrary parametric function with at least n=2 parameters, an exponential function with two free parameters A and B is used to describe the dynamic pressure dependence of the leak flow. The leak flow amounts to $$\dot{V}_L(T) = A \cdot p^B(t) \tag{1}$$

and the leak volume $V_L$ $$V_L = \int \dot{V}_L(t)dt = A \int p^B(t)dt \tag{2}$$

The volume balance $\Delta V$ generally appears from the equation $$\Delta V = V_L + \epsilon = A\int p^B(t)dt + \epsilon, \quad (3)$$

whereby the summand $\epsilon$ denotes irregular breathing. $\Delta V$ is breath-resolved or averaged over several consecutive breaths. In a completely passive, e.g., sedated, patient, $\Delta V$ and $V_L$ are identical.

In the general case, random positive pressure respiration curves p(t) are assumed. The volume balance and the corresponding respiratory tract pressure curve are measured and are stored for each breath, as is shown, for example, in Table 1.

TABLE 1

Measurements in the general case with random pressure curve.

| Volume balance | Pressure time curve |
|---|---|
| $\Delta V_1$ | $p_1(t)$ |
| $\Delta V_2$ | $p_2(t)$ |
| $\Delta V_3$ | $p_3(t)$ |
| ... | ... |

By means of the model statement according to equation 3

$$\Delta V = A\int p^B(t)dt + \epsilon, \quad (4)$$

the free parameters A and B can be estimated by means of using suitable regression methods. The prerequisite for an estimate is that enough breaths ($n \geq 2$) are measured and that the leak volumes and pressure curves, in particular the maximum inspiration pressure, are sufficiently different.

The method can be simplified if each breath is split into N intervals and an average respiratory tract pressure is determined at each of these intervals. The simplification is exact, i.e., a systematic error does not arise if the respiratory tract pressure curve does not deviate from the respective average respiratory tract pressure at the intervals, i.e., if the pressure curve can be described as a step function.

If the simplified case of two intervals (inspiration and expiration) and a step-like pressure curve are taken into account, then $p(t)=p_{insp}$ during the inspiration phase and $p(t)=$peep in the expiration phase.

According to Table 2, the volume balance is determined for each breath both for the inspiration and the expiration.

TABLE 2

Measurements for the simplified method with constant pressure curve in the inspiration phase and the expiration phase.

| Volume balance | Inspiration interval | Expiration interval |
|---|---|---|
| $\Delta V_1$ | $P_{insp1}, T_{insp1}$ | $peep_1, T_{exsp1}$ |
| $\Delta V_2$ | $P_{insp2}, T_{insp2}$ | $peep_2, T_{exsp2}$ |
| $\Delta V_3$ | $P_{insp3}, T_{insp3}$ | $peep_3, T_{exsp3}$ |
| ... | ... | ... |

From the general model statement according to equation 4, $$\Delta V = A \cdot (p_{insp}{}^B \cdot T_{insp} + peep^B \cdot T_{exsp}) + \epsilon \quad (5)$$

is obtained after the simplification.

As in the general case, the free parameters A and B can be estimated by means of suitable regression methods. The regression is then two-dimensional with $p_{insp}$ and peep as regressors. The regression is simpler, if the peep is constant, i.e., if it does not change over the breaths taken into account.

The simplest case is present, if peep=0, since the parameters A and B can be estimated here with linear regression.

According to Table 3, the volume balance and pressure and duration of the inspiration phase are determined for each breath.

TABLE 3

Measurements for the simplest case with rectangular pressure curve during the inspiration ($p_{insp}$) and peep = 0 in the expiration phase

| Volume balance | Inspiration interval |
|---|---|
| $\Delta V_1$ | $P_{insp1}, T_{insp1}$ |
| $\Delta V_2$ | $P_{insp2}, T_{insp2}$ |
| $\Delta V_3$ | $P_{insp3}, T_{insp3}$ |
| ... | ... |

From the model statement according to equation 5, the model $$\Delta V = A \cdot p_{insp}{}^B \cdot T_{insp} + \epsilon \quad (6)$$

is obtained under the simplified marginal conditions (peep=0).

Taking the logarithm of the equation results in $$\log(\Delta V - \epsilon) = \log(A \cdot T_{insp}) + B \log(p_{insp}) \quad (7)$$

and thus the possibility of the simple linear regression for determining the parameters A and B.

With idealized, rectangular pressure curve, the respirator produces a constant excess pressure $P_{insp}$ at the respiratory tract opening of the patient during the inspiration phase with the duration $T_{insp}$. It is assumed that the applied excess pressure falls back to zero in a sufficiently short time after the exchange in the expiration phase, so that $P_{exp}=0$ applies. The excess pressure in the inspiration phase $P_{insp}$ is determinant for the leak occurring there with the leak volume $V_L$, which can be caused by an incorrectly fitted respirator mask, a poorly situated tube or an unintended discharge opening. An $i^{th}$ inspiration phase is described by the pressure $P_{inspi}$, the inspiration time $T_{inspi}$ and by the leak volume $V_{Li}$.

It is assumed that the inspiration pressure $P_{insp}$ can vary from breath to breath. Other examples where $P_{inspi}$ varies from breath to breath are: volume controlled ventilation; and proportional assist ventilation (resp. proportional pressure support). The case of an inspiration pressure that is constant over all breaths taken into account is discussed separately. A measured value each is taken for the pressure $P_{inspi}$ and the inspiration time $T_{inspi}$ for each breath i. The leak volume $V_{Li}$ cannot generally be measured, but can only be estimated. The volume balance $\Delta V_i$ is an estimated value for $V_{Li}$ that is true to expectations and deviates from this only because of physiological irregular breathing $\epsilon_i$. The volume balance $\Delta V_i$ is identical to the leak volume $V_{Li}$ in a passive, e.g., sedated patient.

Irregular breathing $\epsilon$ interferes with a determination of the dependence of the leak volume $V_L$ on the inspiration pressure $P_{insp}$. For this reason, the data of the breaths, which are characterized by significant irregular breathing, are discarded. The irregular breathing $\epsilon$ cannot be measured directly. However, since it is correlated with the expiratory volume $V_{exp}$, the latter can be used as an indicator of the irregular breathing. The breaths, in which the expiratory volume deviates sharply from the "mean value," are discarded. A median-based criterion is used in this case: The breaths, in which the current measured value $V_{expi}$ deviates from the median of the past m measured values by more than a certain percentage (20%), are eliminated.

According to the simplified model, it is assumed that the dependence of the leak flow on the inspiration pressure $P_{insp}$ can be described by means of the exponential function. As in equation 6, the result for the leak volume $V_{Li}$ is:

$$V_{Li} = A \cdot p_{insp_i}^B \cdot T_{insp_i} \tag{8}$$

Since the leak volume $V_{Li}$ is not available as a measured value, the volume balance $\Delta V_i$, interfered with by irregular breathing $\epsilon_i$, is used as an alternative $$\Delta V_i = A \cdot p_{insp_i}^B \cdot T_{insp_i} + \epsilon_i \tag{9}$$

The free parameters of the function A and B can be estimated, e.g., by nonlinear regression or more simply using the following method:

The logarithm is taken of equation (9), and a linear equation is obtained $$\log(\Delta V_i - \epsilon_i) - \log T_{insp} = \log A + B \log p_{insp} \tag{10}$$

in which the irregular breathing $\epsilon_i$ is no longer additive but is in the logarithm. By means of Taylor expansion and termination after the first term, $$\log \Delta V_i - \log T_{inspi} = \log A + B \log p_{inspi} + \epsilon_i / \Delta V_i \tag{11}$$

is obtained approximately.

The left side can be represented abbreviated by $y_i$ and the term $\log(p_{inspi})$ by $x_i$.

It is assumed that the noise term standardized to $\Delta V_i$, i.e., residual irregular breathing standardized to the volume balance, $E_i = \epsilon_i / \Delta V_i$, is random and not dependent on $p_{inspi}$ or $\Delta V_i$. Simplifying, with $a = \log A$, the result is $$y_i = a + B x_i + E_i \tag{12}$$

To determine the constants a and B, only the point of intersection with the y axis and the gradient of the fitted straight lines must be determined. Classical linear regression is suitable for this and yields the following result:

$$B = \frac{\langle x \rangle \langle y \rangle - \langle xy \rangle}{\langle x \rangle \langle x \rangle - \langle xx \rangle} \tag{13}$$

$$a = \langle y \rangle - B \langle x \rangle \quad A = e^{\langle y \rangle - B \langle x \rangle}$$

whereby the brackets represent averaged measured values over several breaths.

With the coefficients A and B now known, the leak flow can be calculated directly from the positive pressure respiration $$\dot{V}_L = A \cdot p^B(t). \tag{14}$$

Since the pressure is constant in both the inspiration phase and the expiration phase for the special simplest case, $$p(t) = \begin{cases} p_{insp} & \text{for inspiration phase} \\ 0 & \text{for expiration phase} \end{cases} \tag{15}$$

applies, and the corresponding result for the leak flow is $$\dot{V}_L(t) = \begin{cases} A \cdot p_{insp}^B & \text{for inspiration phase} \\ 0 & \text{for expiration phase} \end{cases} \tag{16}$$

If the inspiration pressure is constant over all the breaths taken into account, this would be, e.g., the case in conventional respiration with BIPAP at PEEP=0, only two points (zero point and measured point) are available for the regression according to equation 9, through which a fitted curve shall be drawn. Thus, only a linear statement is possible, i.e., the exponent B is arbitrarily The linear statement is given only for the sake of completeness and is not a subject of the present invention.

An exemplary embodiment of the present invention is shown in the drawing and explained in detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
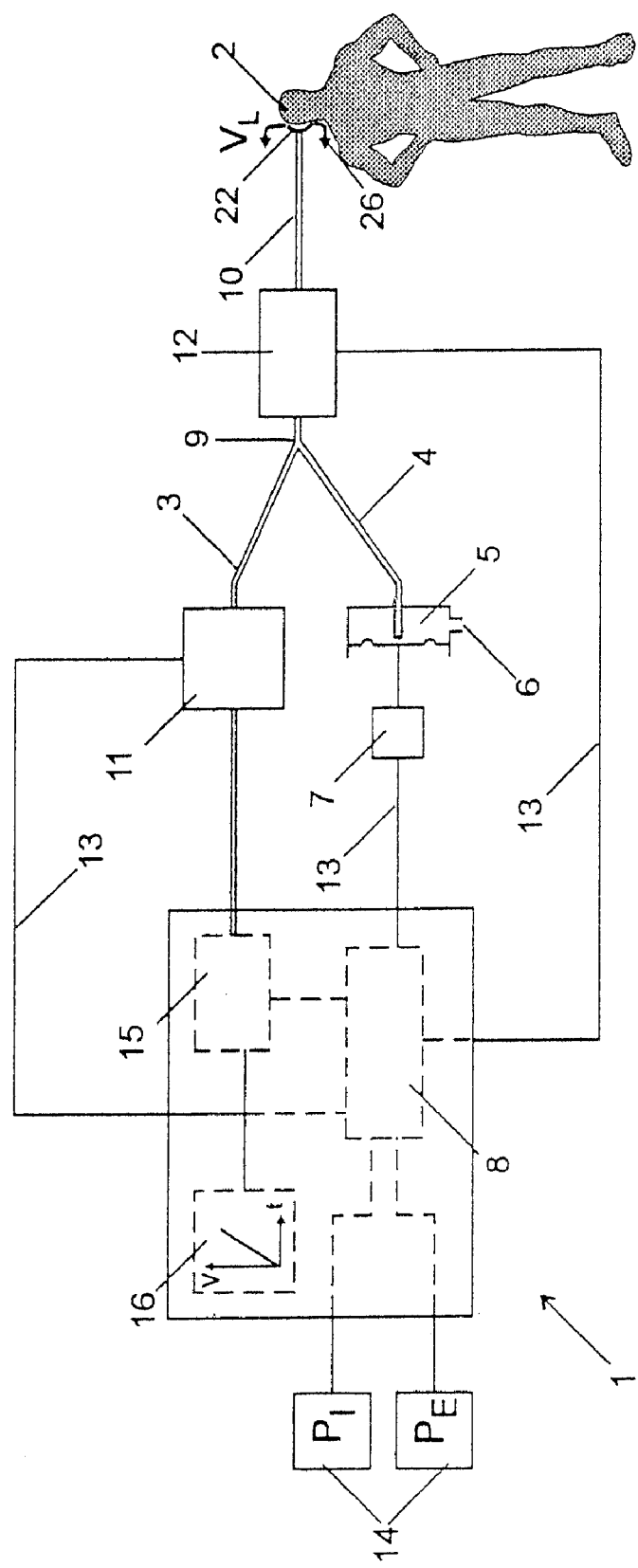
FIG. 1 is a schematic view showing the construction of a respirator with features for practicing the invention.

Referring to the drawings in particular, FIG. 1 shows a respirator 1 for supplying a patient 2 with breathing gas via an inspiration line 3. The exhaled breathing gas reaches an expiration outlet 6 via an expiration line 4 and an expiration valve 5. The expiration valve 5, which sets an expiration pressure $p_{peep}$ during the expiration of the patient, is actuated by a linear drive 7, which is connected to an analyzing unit 8 of the respirator 1 via a signal line 13. The inspiration line 3 and the expiration line 4 merge into a Y piece 9, from which a joint breathing gas line 10 for the inspiration and expiration leads to the patient. A pressure sensor 11 for measuring the breathing gas pressure p and a flow sensor 12 for measuring the breathing gas flow V are arranged in the inspiration line 3 and are connected to the analyzing unit 8 via signal lines 13. The analyzing unit 8 contains a central control unit of the respirator 1 with a microprocessor, which is not shown in detail in FIG. 1, for storing and analyzing the data supplied by the measuring systems 11, 12 and for controlling the breathing phases.

To the analyzing unit 8 is connected a set point transducer 14 for the inspiration pressure $p_{insp}$ and for the expiration pressure $p_{peep}$, which receives the values selected by the user. The breathing gas flow to the patient 2 is dispensed via a control valve 15, which is connected to a pressure gas source, which is not shown in detail in FIG. 1, and receives predetermined values for the inspiration pressure $p_{insp}$ and the expiration pressure $p_{peep}$ from a ramp generator 16 during the inspiration. The leak flow $V_L$ is illustrated by arrows 26 on a leaky breathing mask 22.

Figure 2:
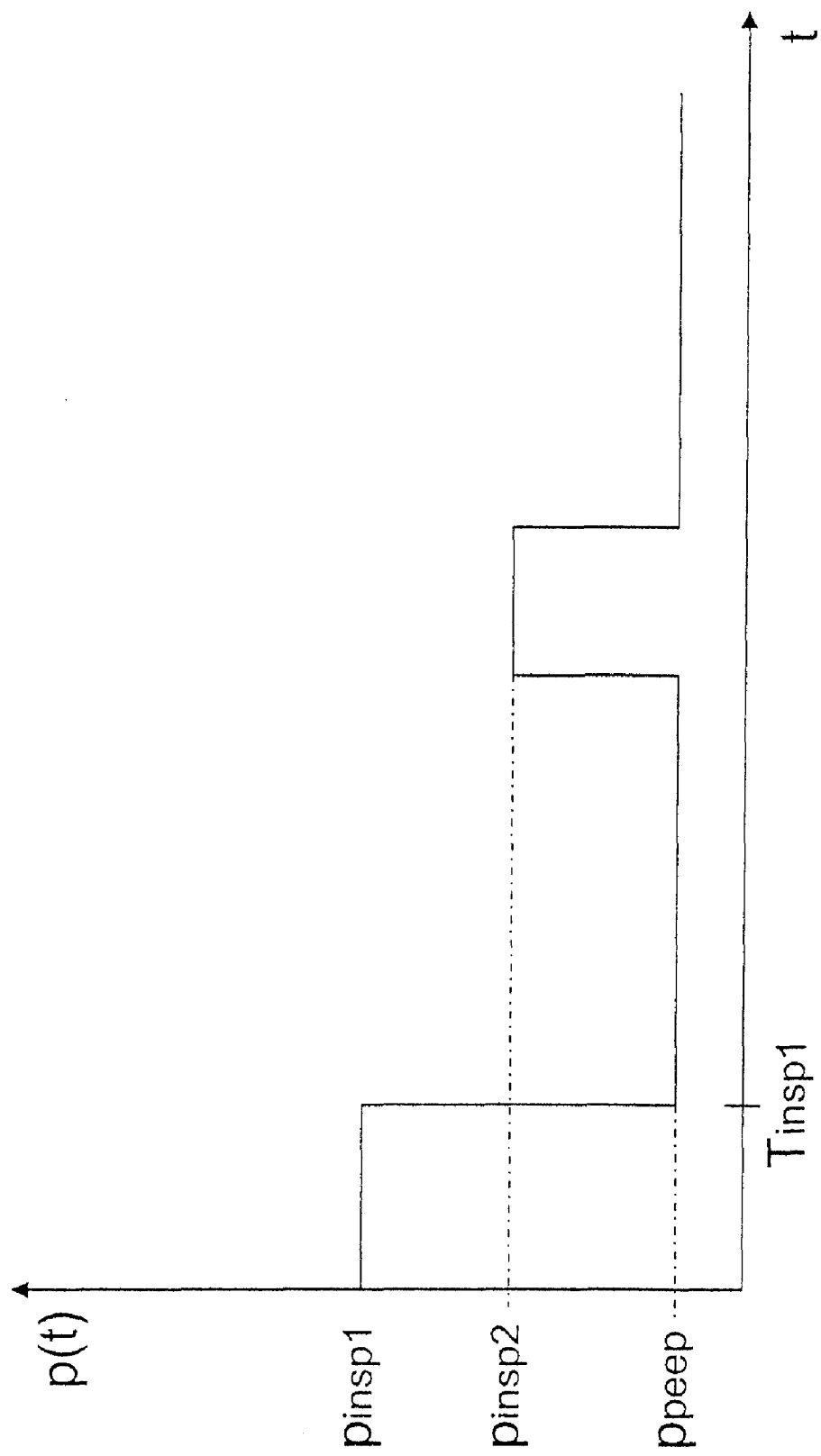
FIG. 2 is a graph showing an example for a rectangular positive pressure respiration curve.

FIG. 2 schematically illustrates the time curve of the breathing gas pressure p(t). An idealized state is assumed, in which both the inspiration pressure $p_{insp}$ and the expiration pressure $p_{peep}$ is constant. Two breathing phases with the inspiration phases $p_{insp1}$ and $p_{insp2}$ and the inspiration time $T_{insp}$ are illustrated.

Figure 3:
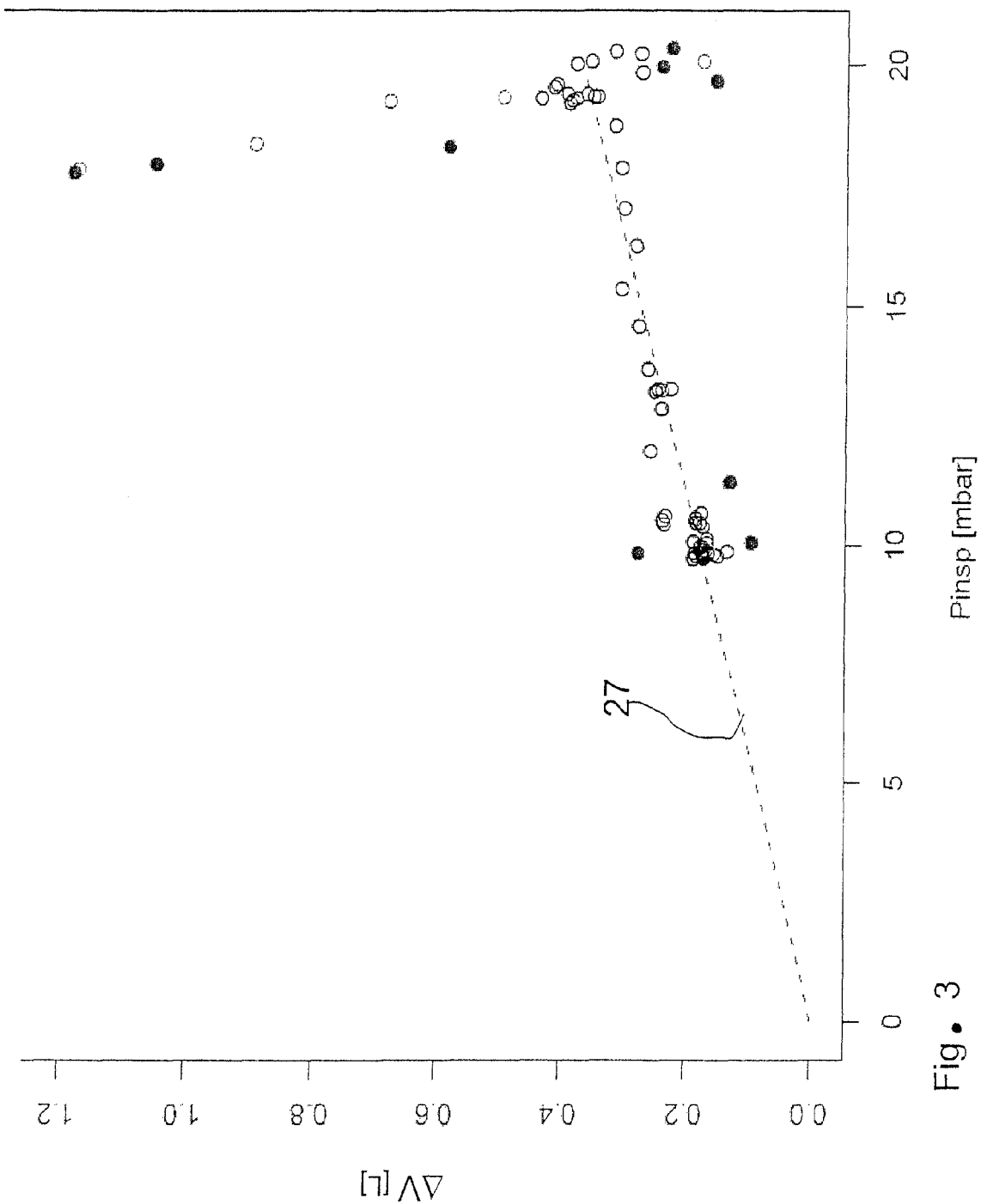
FIG. 3 is a graph showing a first measurement curve for a leak.

FIG. 3 illustrates an example of experimentally determined leaks $\Delta V_i$, which can be approximated by a linear function 27. The freak values shown in the right-hand area of FIG. 3 were eliminated by means of a median-based criterion and were not taken into consideration in the determination of the fitted straight lines.

Figure 4:
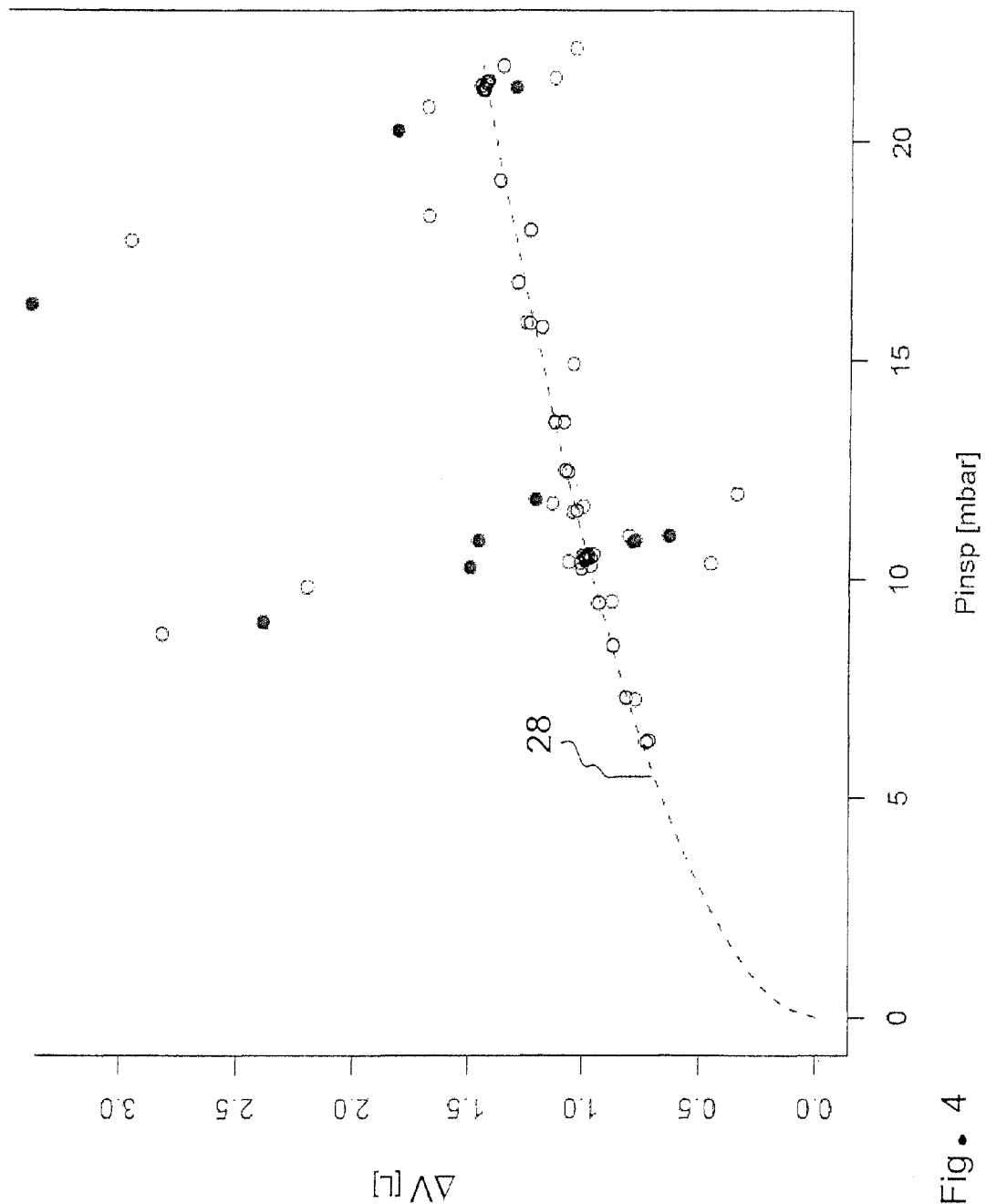
FIG. 4 is a graph showing a second measurement curve for a leak.

FIG. 4 shows another example of measured leak values, whose averaged curve can be described by means of a square root function 28.

Figure 5:
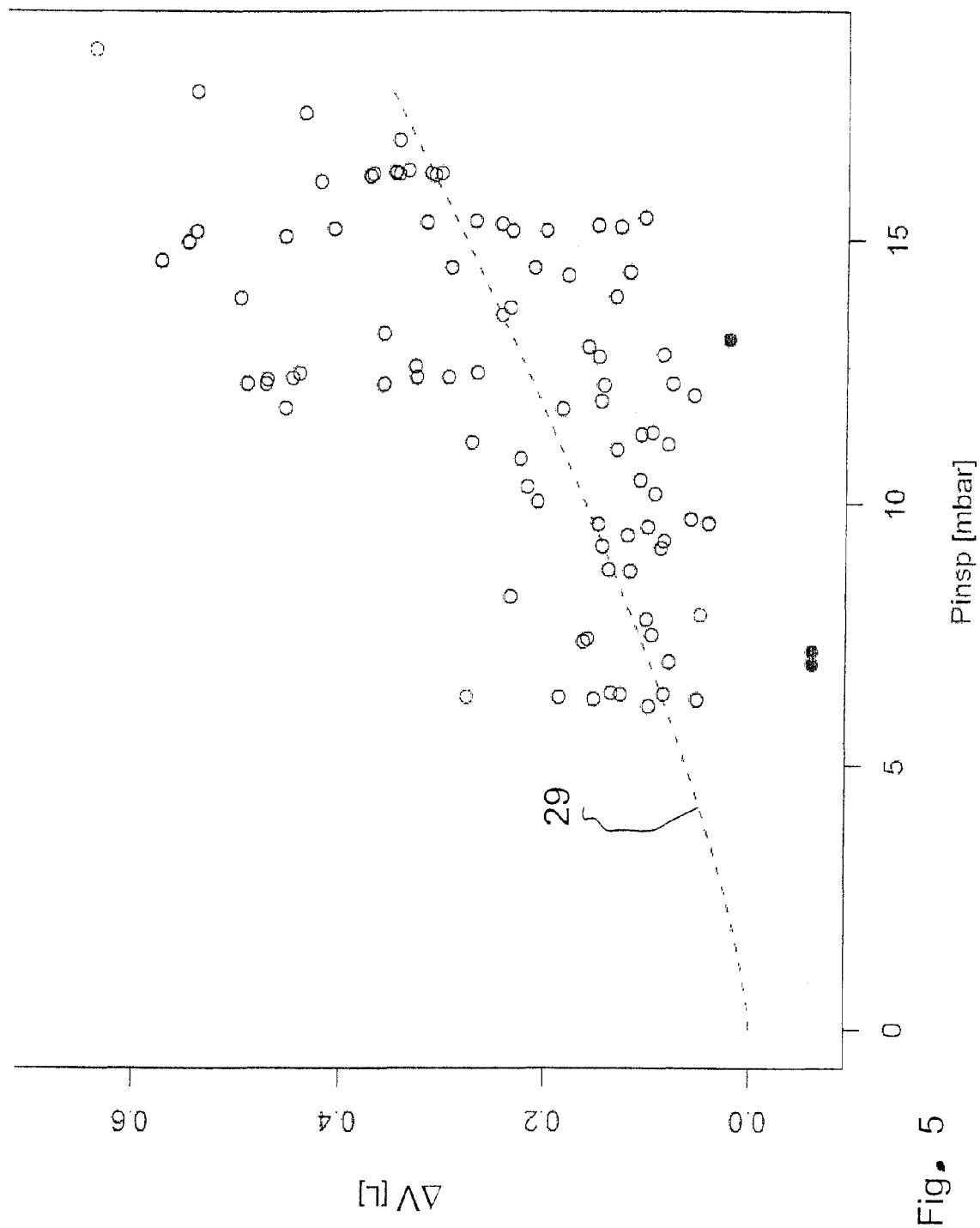
FIG. 5 is a graph showing a third measurement curve for a leak.

FIG. 5 illustrates leak values, which can be approximated by means of a parabolic function 29.

All three examples can be equally described by means of the exponential function given according to the present invention. In this way, a greater range of variation of the approximation, which includes both linear and square root as well as parabolic leak forms, is obtained.

While specific embodiments of the invention have been shown and described in detail to illustrate the application of the principles of the invention, it will be understood that the invention may be embodied otherwise without departing from such principles.

What is claimed is:

1. A method for the determination of leaks in a device for supplying a patient with breathing gas, the method comprising the steps of:
   providing an analyzing unit and a measuring device for determining the respiratory tract pressure;
   recording an inspiration pressure $p_{insp}$ during an inspiration time $T_{insp}$ with the measuring device;
   varying the inspiration pressure $p_{insp}$ during consecutive breaths i;
   determining leak volumes $V_{Li}$ from the product of $p_{inspi}$ and $T_{inspi}$ in accordance with the equation $$V_{Li} = A \times p_{inspi}^B \times T_{inspi}$$

while the parameters A and B are determined in the analyzing unit by a regression model with $p_{insp}$ as the regressor.

2. A method in accordance with claim 1, further comprising the step of adding an additive term $\epsilon_i$, which takes irregular breathing of the patient into consideration, to the equation for $V_{Li}$.

3. A method in accordance with claim 1, further comprising the step of additionally taking into account the end expiratory pressure peep as another regressor and thus allowing variable expiratory pressures according to the equation $$V_{Li} = A(p_{inspi}^B \cdot T_{inspi} + \text{peep}_i^B \cdot T_{exspi}) + \epsilon_i.$$

4. A device for the determination of leaks in a device for supplying a patient with breathing gas, the device comprising:
   a means for producing a respiratory pressure curve;
   a means for switching between an inspiration phase and an expiration phase;
   a measuring device for recording an inspiration pressure $p_{insp}$; and
   a means for determining leak volumes $V_{Li}$ from the product of $p_{inspi}$ and $T_{inspi}$ in accordance with the equation $$V_{Li} = A \times p_{inspi}^B \times T_{inspi}$$

with the parameters A and B to be determined by a regression calculation, wherein said means for determining leak volumes includes determining a leak flow $\dot{V}_L(t)$ from the positive pressure respiration curve p(t) according to the equation $$\dot{V}_L(T) = A \cdot p^B(t)$$

with the parameters A and B to be determined by a regression calculation.

5. A method for the determination of leaks in a device for supplying a patient with breathing gas, the method comprising the steps of:
   providing an analyzing unit and a measuring device for determining the respiratory tract pressure;
   recording an inspiration pressure $p_{insp}$ during an inspiration $T_{insp}$ with the measuring device;
   determining parameters A and B with said regression model in said analyzing unit, wherein $p_{insp}$ is the regressor;
   varying the inspiration pressure $p_{insp}$ during consecutive breaths i;
   determining leak volumes $V_{Li}$ from the product of $p_{inspi}$ and $T_{inspi}$ based on the equation $$V_{Li} = A \times p_{inspi}^B \times T_{inspi}.$$

6. A method in accordance with claim 5, further comprising the step of additionally taking into account the end expiratory pressure peep as another regressor and thus allowing variable expiratory pressures according to the equation $$V_{Li} = A(p_{inspi}^B \cdot T_{inspi} + \text{peep}_i^B \cdot T_{inspi}) + \epsilon_i.$$

7. A method in accordance with claim 6, further comprising:
   determining an expiratory volume for each breathe to provide a plurality of expiratory volume values;
   calculating a mean value based on said plurality of expiratory volume values;
   determining whether one or more measured expiratory volume values is above a predetermined deviation range with respect to said mean value to define one or more irregular breathing values, wherein said step of determining said leak volumes $V_{Li}$ does not include said irregular breathing values.

8. A method in accordance with claim 3, further comprising:
   determining an expiratory volume for each breathe to provide a plurality of expiratory volume values;
   calculating a mean value based on said plurality of expiratory volume values;
   determining whether one or more measured expiratory volume values is above a predetermined deviation range with respect to said mean value to define one or more irregular breathing values, wherein said step of determining said leak volumes $V_{Li}$ does not include said irregular breathing values.

* * * * *